(12) United States Patent
Struthers et al.

(10) Patent No.: US 12,076,548 B2
(45) Date of Patent: Sep. 3, 2024

(54) BLOOD PUMP WITH PIVOTABLE HOUSING

(71) Applicant: Boston Scientific Scimed Inc, Maple Grove, MN (US)

(72) Inventors: Brett Struthers, Victoria, MN (US); Thomas P. Jancaric, Maple Grove, MN (US); Matthew Boyer, Columbia Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 713 days.

(21) Appl. No.: 17/189,932

(22) Filed: Mar. 2, 2021

(65) Prior Publication Data

US 2021/0275796 A1 Sep. 9, 2021

Related U.S. Application Data

(60) Provisional application No. 62/984,327, filed on Mar. 3, 2020.

(51) Int. Cl.
*A61M 60/216* (2021.01)
*A61M 60/419* (2021.01)
*A61M 60/804* (2021.01)

(52) U.S. Cl.
CPC ........ *A61M 60/216* (2021.01); *A61M 60/419* (2021.01); *A61M 60/804* (2021.01)

(58) Field of Classification Search
CPC . A61M 60/216; A61M 60/419; A61M 60/804
See application file for complete search history.

(56) References Cited

U.S. PATENT DOCUMENTS

| 8,489,190 B2 | 7/2013 | Pfeffer et al. |
| 9,421,311 B2 | 8/2016 | Tanner et al. |
| 9,533,084 B2 | 1/2017 | Siess et al. |
| 10,478,538 B2 | 11/2019 | Scheckel et al. |
| 10,576,193 B2 | 3/2020 | Tanner et al. |
| 10,583,232 B2 * | 3/2020 | Muller ................ A61M 60/515 |
| 10,780,206 B2 | 9/2020 | Shambaugh et al. |
| 10,905,808 B2 | 2/2021 | Tuval et al. |
| 11,202,900 B2 | 12/2021 | Higgins et al. |
| 11,460,030 B2 | 10/2022 | Shambaugh et al. |
| 11,517,736 B2 | 12/2022 | Earles et al. |
| 11,571,559 B2 | 2/2023 | Clifton et al. |
| 11,666,748 B2 | 6/2023 | Kronstedt et al. |
| 11,697,017 B2 | 7/2023 | Clifton et al. |
| 2020/0306434 A1 | 10/2020 | VanCamp et al. |
| 2021/0077680 A1 | 3/2021 | Tanner et al. |
| 2021/0077684 A1 | 3/2021 | Tanner et al. |
| 2021/0220636 A1 | 7/2021 | Schauer et al. |

(Continued)

FOREIGN PATENT DOCUMENTS

DE      102020102473 A1 *  8/2021

*Primary Examiner* — Ariana Zimbouski
*Assistant Examiner* — Jacob Lee Fincher
(74) *Attorney, Agent, or Firm* — Seager, Tufte & Wickhem LLP

(57) ABSTRACT

Various aspects of the present invention are directed towards apparatuses, systems, and methods that may include a blood pump. The blood pump may include an impeller assembly housing, an impeller assembly having an impeller configured to cause blood to flow through the pump, a motor housing, a motor configured to drive the impeller, and a pivotable housing connector.

17 Claims, 3 Drawing Sheets

(56) References Cited

U.S. PATENT DOCUMENTS

2021/0220637 A1    7/2021  Edwards et al.
2021/0275796 A1    9/2021  Struthers et al.
2022/0233757 A1*   7/2022  Visser ................. A61M 60/174

* cited by examiner

BLOOD PUMP WITH PIVOTABLE HOUSING

CROSS REFERENCE TO RELATED APPLICATION

This application claims priority to Provisional Application No. 62/984,327, filed Mar. 3, 2020, which is herein incorporated by reference in its entirety.

TECHNICAL FIELD

The present disclosure relates to percutaneous circulatory support devices. More specifically, the disclosure relates to flexible housing designs used in percutaneous circulatory support devices.

BACKGROUND

Due to the tortuosity of human aortas, the curve of the aortic arch may pose challenges during and post-delivery of circulatory support devices. Moreover, delivering a device that is too large and/or rigid to fit the curve of the aortic arch could harm both the patient and the device.

SUMMARY

In Example 1, a blood pump includes an impeller assembly housing; an impeller assembly disposed within the impeller assembly housing and having an impeller configured to cause blood to flow through the pump; a motor housing; a motor disposed within the motor housing and configured to drive the impeller; and a pivotable housing connector coupled to the motor housing and the impeller assembly housing.

In Example 2, the blood pump of Example 1, includes the pivotable housing connector includes a first portion and a second portion, the first portion is coupled to the second portion by a mechanical pivot joint.

In Example 3, the blood pump of Example 1, the pivotable housing connector includes a flexible membrane.

In Example 4, the blood pump of any of Examples 1-3, further includes one or more steering wires coupled, at a distal end, to the impeller assembly housing, and, at a proximal end, to a control mechanism, the one or more steering wires passing through the pivotable housing connector and configured to facilitate adjusting a position of the impeller assembly housing.

In Example 5, the blood pump of any of Examples 1-4, the motor includes a driving magnet assembly and the impeller assembly includes a driven magnet assembly coupled to the impeller and configured to rotate with the impeller, the driving magnet assembly is configured to cause the driven magnet assembly to rotate.

In Example 6, the blood pump of Example 5, the driving magnet assembly includes a primary driving surface and the driven magnet assembly includes a primary driven surface, the primary driving surface and primary driven surface are configured so that the driving magnet assembly and the driven magnet assembly achieve a maximum magnetic coupling when the impeller assembly housing is in a coupling position with respect to the motor housing.

In Example 7, the blood pump of Example 6, when the impeller assembly is in the coupling position, the primary driving surface is parallel to the primary driven surface.

In Example 8, the blood pump of either of Example 6 or 7, further includes a pivot stop configured to prevent the impeller assembly housing from moving beyond the coupling position.

In Example 9, the blood pump of any of Examples 6-8, the impeller assembly housing is configured to be moved into one or more additional coupling positions, each of the one or more additional coupling positions corresponding to a specified torque response.

In Example 10, a blood pump includes an impeller assembly housing; an impeller assembly disposed within the impeller assembly housing and having an impeller configured to cause blood to flow through the pump; a motor housing; a motor disposed within the motor housing and configured to drive the impeller; and a pivotable housing connector coupled to the motor housing and the impeller assembly housing, the impeller assembly housing is configured to be moved into one or more coupling positions, each of the one or more coupling positions corresponding to a specified torque response.

In Example 11, the blood pump of Example 10, the pivotable housing connector includes a mechanical pivot joint or a flexible membrane.

In Example 12, the blood pump of either of Example 10 or 11, the motor includes a driving magnet assembly and the impeller assembly includes a driven magnet assembly coupled to the impeller and configured to rotate with the impeller, the driving magnet assembly is configured to cause the driven magnet assembly to rotate.

In Example 13, the blood pump of Example 12, the driving magnet assembly includes a primary driving surface and the driven magnet assembly includes a primary driven surface, the primary driving surface and primary driven surface are configured so that the driving magnet assembly and the driven magnet assembly achieve a maximum magnetic coupling when the impeller assembly housing is in a first coupling position with respect to the motor housing.

In Example 14, the blood pump of Example 13, when the impeller assembly is in the first coupling position, the primary driving surface is parallel to the primary driven surface.

In Example 15, the blood pump of any of Examples 10-14, further includes a pivot stop configured to hold the impeller assembly in one of the one or more coupling positions.

In Example 16, a blood pump includes an impeller assembly housing; an impeller assembly disposed within the impeller assembly housing and having an impeller configured to cause blood to flow through the pump; a motor housing; a motor disposed within the motor housing and configured to drive the impeller; and a pivotable housing connector coupled, at a first end, to a distal end of the motor housing and, at a second end, to a proximal end of the impeller assembly housing.

In Example 17, the blood pump of Example 16, the pivotable housing connector includes a first portion and a second portion, the first portion is coupled to the second portion by a mechanical pivot joint.

In Example 18, the blood pump of Example 16, the pivotable housing connector includes a flexible membrane.

In Example 19, the blood pump of any of Examples 16-18, further includes one or more steering wires coupled, at a distal end, to the impeller assembly housing, and, at a proximal end, to a control mechanism, the one or more steering wires passing through the pivotable housing connector and configured to facilitate adjusting a position of the impeller assembly housing.

In Example 20, the blood pump of any of Examples 16-19, the motor includes a driving magnet assembly and the impeller assembly includes a driven magnet assembly coupled to the impeller and configured to rotate with the impeller, the driving magnet assembly is configured to cause the driven magnet assembly to rotate.

In Example 21, the blood pump of Example 20, the driving magnet assembly includes a primary driving surface and the driven magnet assembly includes a primary driven surface, the primary driving surface and primary driven surface are configured so that the driving magnet assembly and the driven magnet assembly achieve a maximum magnetic coupling when the impeller assembly housing is in a coupling position with respect to the motor housing.

In Example 22, the blood pump of Example 21, when the impeller assembly is in the coupling position, the primary driving surface is parallel to the primary driven surface.

In Example 23, the blood pump of either of Example 21 or 22, further includes a pivot stop configured to prevent the impeller assembly housing from moving beyond the coupling position.

In Example 24, the blood pump of any of Examples 21-23, the impeller assembly housing is configured to be moved into one or more additional coupling positions, each of the one or more additional coupling positions corresponding to a specified torque response.

In Example 25, a blood pump includes an impeller assembly housing; an impeller assembly disposed within the impeller assembly housing and having an impeller configured to cause blood to flow through the pump; a motor housing; a motor disposed within the motor housing and configured to drive the impeller; and a pivotable housing connector coupled, at a first end, to a distal end of the motor housing and, at a second end, to a proximal end of the impeller assembly housing, the impeller assembly housing is configured to be moved into one or more coupling positions, each of the one or more coupling positions corresponding to a specified torque response.

In Example 26, the blood pump of Example 25, the pivotable housing connector includes a mechanical pivot joint or a flexible membrane.

In Example 27, the blood pump of Example 25, the motor includes a driving magnet assembly and the impeller assembly includes a driven magnet assembly coupled to the impeller and configured to rotate with the impeller, the driving magnet assembly is configured to cause the driven magnet assembly to rotate.

In Example 28, the blood pump of Example 27, the driving magnet assembly includes a primary driving surface and the driven magnet assembly includes a primary driven surface, the primary driving surface and primary driven surface are configured so that the driving magnet assembly and the driven magnet assembly achieve a maximum magnetic coupling when the impeller assembly housing is in a first coupling position with respect to the motor housing.

In Example 29, the blood pump of Example 28, when the impeller assembly is in the first coupling position, the primary driving surface is parallel to the primary driven surface.

In Example 30, the blood pump of Example 29, further including a pivot stop configured to hold the impeller assembly in each of the one or more coupling positions.

In Example 31, the blood pump of Example 25, further includes one or more steering wires coupled, at a distal end, to the impeller assembly housing, and, at a proximal end, to a control mechanism, the one or more steering wires passing through the pivotable housing connector and configured to facilitate adjusting a position of the impeller assembly housing.

In Example 32, a blood pump includes an impeller assembly housing; an impeller assembly disposed within the impeller assembly housing and having an impeller configured to cause blood to flow through the pump; a motor housing; a motor disposed within the motor housing and configured to drive the impeller; and a pivotable housing connector coupled, at a first end, to a distal end of the motor housing and, at a second end, to a proximal end of the impeller assembly housing, the pivotable housing connector includes a flexible membrane.

In Example 33, the blood pump of Example 32, the impeller assembly housing is configured to be moved into one or more coupling positions, each of the one or more coupling positions corresponding to a specified torque response.

In Example 34, the blood pump of Example 33, the motor includes a driving magnet assembly and the impeller assembly includes a driven magnet assembly coupled to the impeller and configured to rotate with the impeller, the driving magnet assembly is configured to cause the driven magnet assembly to rotate.

In Example 35, the blood pump of Example 34, the driving magnet assembly includes a primary driving surface and the driven magnet assembly includes a primary driven surface, the primary driving surface and primary driven surface are configured so that the driving magnet assembly and the driven magnet assembly achieve a maximum magnetic coupling when the impeller assembly housing is in a coupling position with respect to the motor housing.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1A:
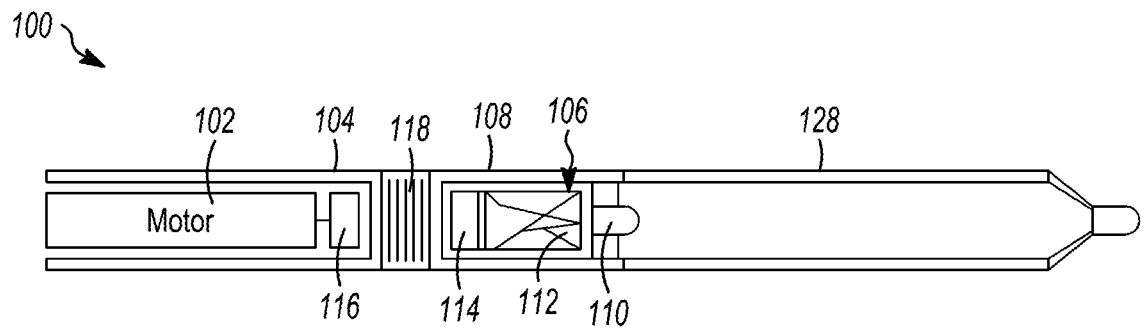
FIGS. 1A and 1B depict a cross-sectional side view of a portion of an illustrative percutaneous mechanical circulatory support device (also referred to herein, interchangeably, as a "blood pump"), in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

DETAILED DESCRIPTION

Figure 1B:
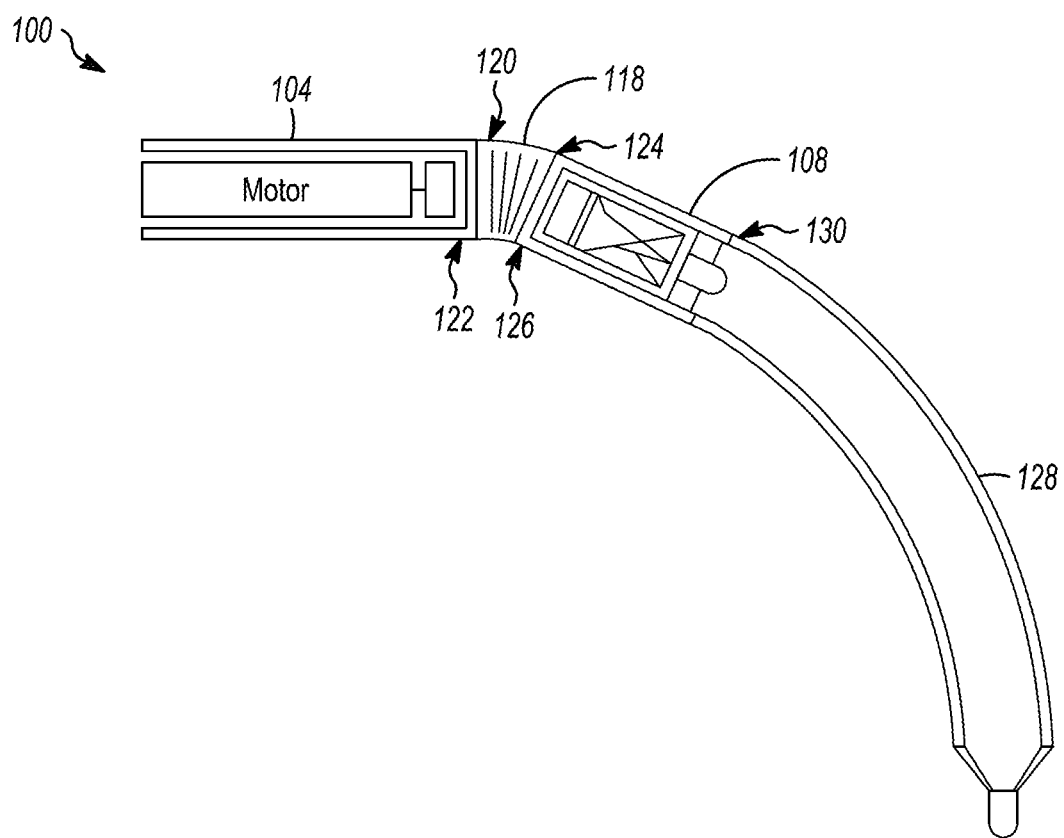

FIGS. 1A and 1B depict a cross-sectional side view of a portion of an illustrative percutaneous mechanical circulatory support device 100 (also referred to herein, interchangeably, as a "blood pump"), in accordance with embodiments of the subject matter disclosed herein. As shown in FIG. 1A, the circulatory support device 100 includes a motor 102 disposed within a motor housing 104. The motor 102 is configured to drive an impeller assembly 106 to provide a flow of blood through the device 100. The impeller assembly 106 is disposed within an impeller assembly housing 108, which includes a number of outlet apertures (not shown) defined therein. According to embodiments, the motor housing 104 and the impeller assembly housing 108 may be integrated with one another. In other embodiments, the motor housing 104 and the impeller assembly housing 108 may be separate components configured to be coupled together, either removeably or permanently.

A controller (not shown) is operably coupled to the motor 102 and is configured to control the motor 102. The controller may be disposed within the motor housing 104 in embodiments, or, in other embodiments, may be disposed outside the housing 104 (e.g., in a catheter handle, independent housing, etc.). In embodiments, the controller may include multiple components, one or more of which may be disposed within the housing 104. According to embodiments, the controller may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like.

As shown in FIG. 1A, the impeller assembly 106 includes a drive shaft 110 and an impeller 112 coupled thereto, where the drive shaft 110 is configured to rotate with the impeller 112. As shown, the drive shaft 110 is at least partially disposed within the impeller 112. In embodiments, the drive shaft 110 may be made of any number of different rigid materials such as, for example, steel, titanium alloys, cobalt chromium alloys, nitinol, high-strength ceramics, and/or the like. In embodiments, the motor 102 may be a direct drive motor and the drive shaft 110 may be rotated by the motor 102 and, in turn, cause the impeller 112 to rotate.

In other embodiments, as shown in FIGS. 1A and 1B, the motor 102 may be a magnetic drive motor, in which case, the impeller assembly 106 may further include an impeller rotor 114 coupled to, and at least partially surrounding, the drive shaft 110. The impeller rotor 114 may be any type of magnetic rotor capable of being driven by a stator 116 that is part of the motor 102. In this manner, as a magnetic field is applied to the impeller rotor 114 by the stator 116 in the motor 102, the rotor 114 rotates, causing the drive shaft 110 and impeller 112 to rotate. Although not illustrated in FIGS. 1A and 1B, the impeller assembly 106 may be maintained in its orientation by the drive shaft 110, which may be retained by one or more bearing assemblies.

As is further shown in FIGS. 1A and 1B, the blood pump includes a pivotable housing connector 118 disposed between the motor housing 104 and the impeller assembly housing 108. That is, for example, the pivotable housing connector 118 is coupled, at a first end 120, to a distal end 122 of the motor housing 104 and, at a second end 124, to a proximal end 126 of the impeller assembly housing 108. According to embodiments, the pivotable housing connector 118 may be configured to enable the impeller assembly housing 108 to pivot with respect to the motor housing 104 in two or three dimensions. In embodiment, the pivotable housing connector 118 may be a flexible membrane, in which case, the pivotable housing connector 118 may be able to bend in any number of different directions, while in other embodiments, the pivotable housing connector 118 may be a mechanical pivot joint configured to allow movement in one or more discrete directions. In embodiments, the flexible membrane may be made of any number of a variety of materials such as, for example, an accordion-like semi-rigid membrane material that allows deflection radially but retains push of the device axially over a wire, a polymer-covered laser cut hypo tube, and/or the like.

As is further shown in FIGS. 1A and 1B, the device 100 may include a flexible inlet tube 128 coupled to a distal end 130 of the impeller assembly housing 108. Due to the flexibility of the inlet tube 128 and the pivotability of the pivotable housing connector 118, embodiments allow the device to conform to the aortic arch shape better than a rigid straight device, facilitating easy deliverability and traceability over the aortic arch. According to embodiments, the drive system of the device may be configured such that the device can operate while in a bent configuration, as described in more detail below, with reference to FIGS. 2A, 2B, 3A, and 3B.

Embodiments of the circulatory support device 100 may also include a steering mechanism. For example, in embodiments, the circulatory support device 100 may include one or more steering wires coupled, at a distal end, to the impeller assembly housing and/or the inlet tube, and, at a proximal end, to a control mechanism, the one or more steering wires passing through the pivotable housing connector 118 and configured to facilitate adjusting a position of the impeller assembly housing and/or the inlet tube. For example, a single or multi-lumen catheter and cannula body may allow tensile cables to extend the length of the pump and counteract to steer the product around difficult vascular tortuosity. Embodiments of this steering mechanism may allow the physician to actively mold the circulatory device to the shape necessary for delivery, operation, or fixturing the device in the aorta. This would provide a custom experience, as the physician could manipulate the device according to each patient's needs.

The illustrative circulatory support device 100 shown in FIGS. 1A and 1B is not intended to suggest any limitation as to the scope of use or functionality of embodiments of the present disclosure. The illustrative circulatory support device 100 also should not be interpreted as having any dependency or requirement related to any single component or combination of components illustrated therein. Additionally, various components depicted in FIGS. 1A and 1B may be, in embodiments, integrated with various ones of the other components depicted therein (and/or components not illustrated), all of which are considered to be within the ambit of the present disclosure.

As explained above, with reference to FIGS. 1A and 1B, in embodiments, the pivotable housing connector divides the rigid length of the circulatory support device roughly in half, separating the halves of the housing which contain the motor and the impeller via a flexible connection. By isolating the motor from the impeller in an enclosed housing, the motor is protected from corrosive biological factors that may shorten the lifespan of the motor. In embodiments, the use of a magnetic drive allows the motor to deliver torque to the impeller, even while the pump housing conforms to the tortuous anatomy within the patient's aorta. The robustness and efficiency of the magnetic coupling would be dependent on the design of the coupling magnets. In embodiments, certain magnet designs would maintain adequate pump torque even while the device translates radially due to force on the distal or proximal ends of the device.

Figure 2A:
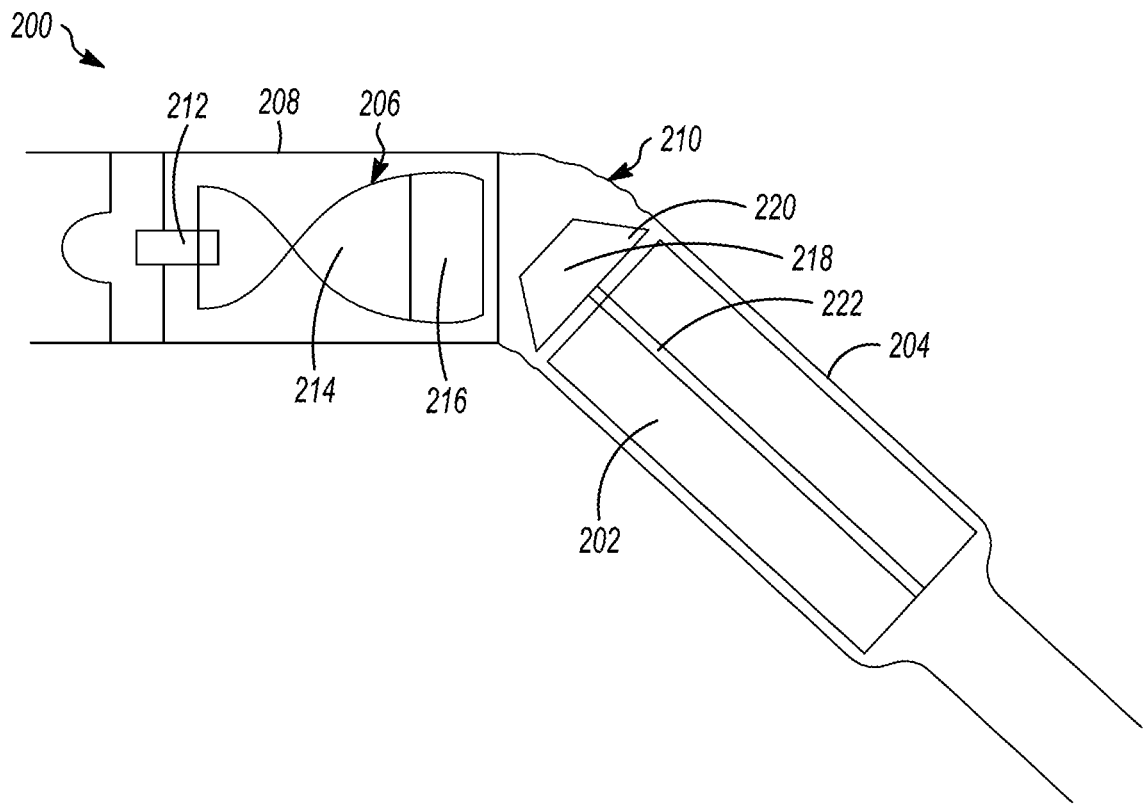
FIG. 2A depicts a cross-sectional side view of an illustrative percutaneous mechanical circulatory support device, in accordance with embodiments of the subject matter disclosed herein.
Figure 2B:
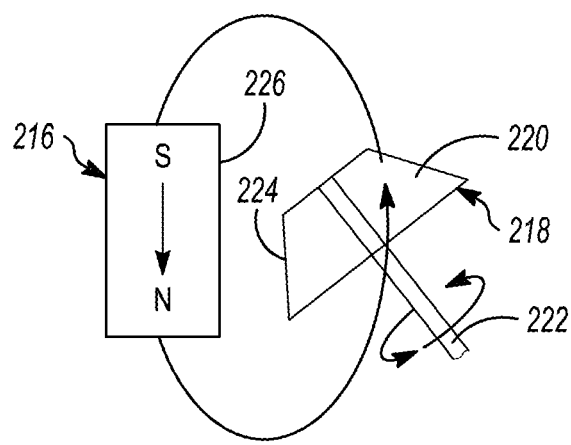
FIG. 2B depicts a schematic side view of a portion of the circulatory support device depicted in FIG. 2A, in accordance with embodiments of the subject matter disclosed herein.

For example, FIG. 2A depicts a cross-sectional side view of an illustrative percutaneous mechanical circulatory support device 200, in accordance with embodiments of the subject matter disclosed herein; and FIG. 2B depicts a schematic side view of a portion of the circulatory support device 200 depicted in FIG. 2A, in accordance with embodiments of the subject matter disclosed herein. According to embodiments, the circulatory support device 200, and/or any number of various components thereof, may be the same as, or similar to, corresponding components of the circulatory support device 100 depicted in FIGS. 1A and 1B.

As shown in FIG. 2A, the circulatory support device 200 includes a motor 202 disposed within a motor housing 204. The motor 202 is configured to drive an impeller assembly 206 to provide a flow of blood through the device 200. The impeller assembly 206 is disposed within an impeller assembly housing 208, which includes a number of inlet apertures (not shown) and a number of outlet apertures (not shown) defined therein. According to embodiments, the motor housing 204 and the impeller assembly housing 208 are separate components configured to be coupled together via a pivotable housing connector 210. A controller (not shown) is operably coupled to the motor 202 and is configured to control the motor 202. The controller may be disposed within the motor housing 204 in embodiments, or, in other embodiments, may be disposed outside the housing 204 (e.g., in a catheter handle, independent housing, etc.). In embodiments, the controller may include multiple components, one or more of which may be disposed within the housing 204. According to embodiments, the motor 204 may be, be similar to, include, or be included in the motor 104 depicted in FIG. 1A.

As shown in FIG. 2A, the impeller assembly 206 includes a drive shaft 212 and an impeller 214 coupled thereto, where the drive shaft 212 is configured to rotate with the impeller 214. As shown, the drive shaft 212 is at least partially disposed within the impeller 214. In embodiments, the drive shaft 212 may be made of any number of different rigid materials such as, for example, steel, titanium alloys, cobalt chromium alloys, nitinol, high-strength ceramics, and/or the like. The impeller assembly 206 further includes a driven magnet 216 coupled to, and at least partially surrounding, the drive shaft 212 and/or the impeller 214. The driven magnet 216 may be any type of magnetic rotor capable of being driven by a driving magnet assembly 218. In this manner, as a magnetic field is applied to the driven magnet 216 by the driving magnet assembly 218, the driven magnet 216 rotates, causing the drive shaft 212 and impeller 214 to rotate.

As shown in FIGS. 2A and 2B, the driving magnet assembly 218 includes a driving magnet 220 coupled to a drive line 222 configured to transfer torque from the motor 202 to the driving magnet 220. The driving magnet 220 includes a primary driving surface 224 and the driven magnet 216 includes a corresponding primary driven surface 226. In embodiments, the primary driving surface 224 and the primary driven surface 226 are configured so that the driving magnet 220 and the driven magnet 216 achieve a maximum magnetic coupling when the impeller assembly housing 208 is in a coupling position with respect to the motor housing 204. In embodiments, the coupling position may be a position in which the pivotable housing connector 210 is pivoted or bent to a specified angle corresponding to characteristics of the anatomy at which the device 200 is to be implanted.

In embodiments, for example, the driven magnet 216 and driving magnet 220 may be configured such that when the impeller assembly housing 208 is in the coupling position, the primary driving surface 224 is parallel to the primary driven surface 226, or at least approximately parallel. Any number of different configurations and designs may be used for the magnets. In embodiments, the device 200 may include a pivot stop (not shown) configured to prevent the impeller assembly housing 208 from moving beyond the coupling position. The pivot stop may be a mechanical mechanism such as a lever, flange, or other blocking, or at least approximately blocking, locking, or otherwise stopping feature. In embodiments, the impeller assembly housing 208 may be configured to be moved into one or more additional coupling positions, each of the one or more additional coupling positions corresponding to a specified torque response from the driven magnet 216 and driving magnet 220, based on the respective orientations thereof. Software may be programmed to account for the geometries of the magnets, the resulting coupling magnetic fields and torque responses corresponding thereto and may be used to adjust the operation of the motor to maintain sufficient coupling as the device is pivoted at the pivotable housing connector 210.

The illustrative circulatory support device 200 shown in FIGS. 2A and 2B is not intended to suggest any limitation as to the scope of use or functionality of embodiments of the present disclosure. The illustrative circulatory support device 200 also should not be interpreted as having any dependency or requirement related to any single component or combination of components illustrated therein. Additionally, various components depicted in FIGS. 2A and 2B may be, in embodiments, integrated with various ones of the other components depicted therein (and/or components not illustrated), all of which are considered to be within the ambit of the present disclosure.

Figure 3A:
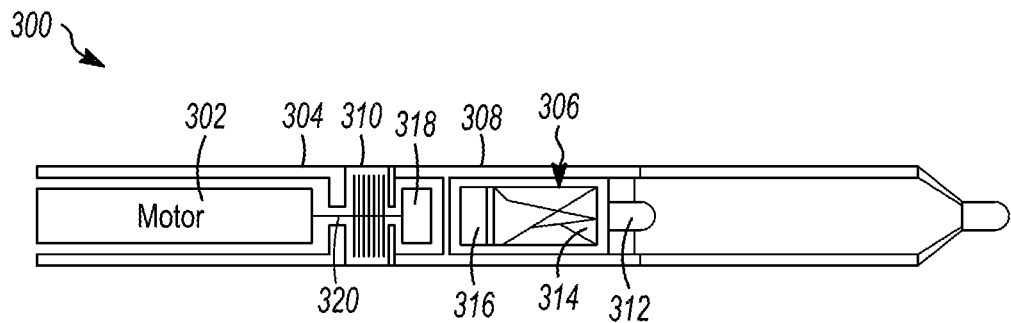
FIGS. 3A and 3B depict a cross-sectional side view of a portion of an illustrative percutaneous mechanical circulatory support device, in accordance with embodiments of the subject matter disclosed herein.
Figure 3B:
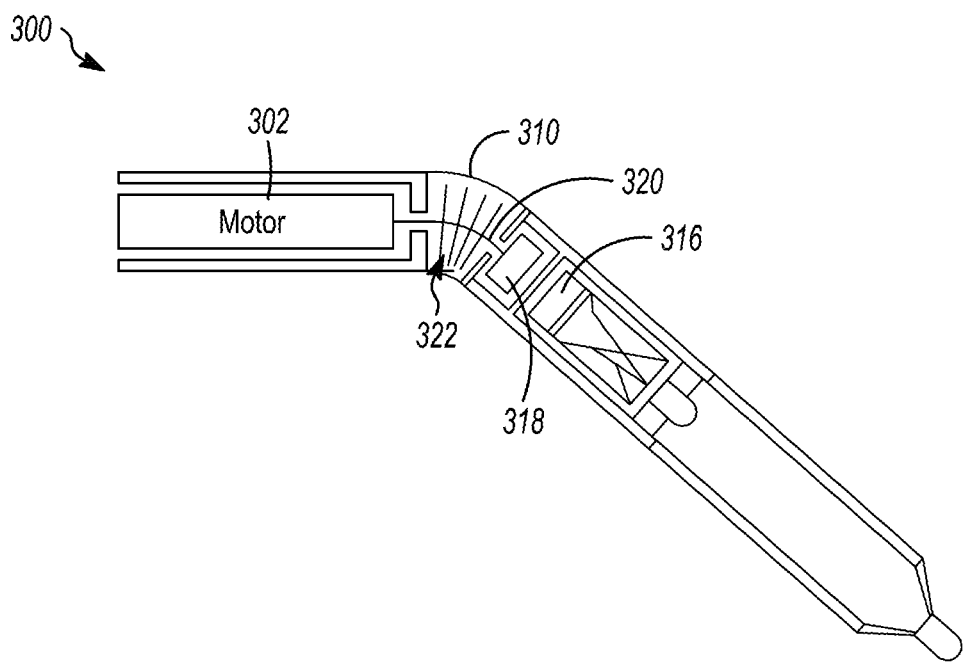

As explained above, magnetic coupling may be used to transfer torque from the motor to the impeller across the pivotable housing connector. According to embodiments, any number of other types of drive technology may be used to transfer the torque. For example, in embodiments, the motor may be a direct drive motor configured to drive a flexible drive shaft (e.g., a drive line) that passes through the pivotable housing connector. In embodiments, to preserve the benefits of using a magnetic drive (e.g., sealing the driving magnet from the blood flow, etc.), a flexible drive line may be used. For example, FIGS. 3A and 3B depict a cross-sectional side view of a portion of an illustrative percutaneous mechanical circulatory support device 300 (also referred to herein, interchangeably, as a "blood pump"), in accordance with embodiments of the subject matter disclosed herein. Any number of aspects of the circulatory support device 300 may be the same as, or similar to, corresponding aspects described above with reference to FIGS. 1A, 1B, 2A, and 2B.

As shown in FIG. 3A, the circulatory support device 300 includes a motor 302 disposed within a motor housing 304. The motor 302 is configured to drive an impeller assembly 306 to provide a flow of blood through the device 300. The impeller assembly 306 is disposed within an impeller assembly housing 308, which includes a number of outlet apertures (not shown) defined therein. The impeller assembly housing 308 is pivotably coupled to the motor housing 304 via a pivotable housing connector 310.

As shown in FIGS. 3A and 3B, the impeller assembly 306 includes a drive shaft 312 and an impeller 314 coupled thereto, where the drive shaft 312 is configured to rotate with the impeller 314. The impeller assembly 306 may further include a driven magnet 316 coupled to at least one of the drive shaft 312 and the impeller 314. The driven magnet 316 may be any type of magnetic rotor capable of being driven by a driving magnet 318. As shown, the motor 302 includes a flexible drive line 320 coupled to the motor 302, extending through an interior chamber 322 of the pivotable housing connector 310, and coupled to the driving magnet 318. The flexible drive line 320 is configured to be caused to rotate by the motor and, in turn, rotate the driving magnet 318 which, in the illustrated embodiment, is disposed in the impeller assembly housing 308. In other embodiments, both the driving magnet and the driven magnet may be disposed in the motor housing and a flexible drive shaft may extend through the pivotable housing connector to the impeller in the impeller assembly housing.

The illustrative circulatory support device 300 shown in FIGS. 3A and 3B is not intended to suggest any limitation as to the scope of use or functionality of embodiments of the present disclosure. The illustrative circulatory support device 300 also should not be interpreted as having any dependency or requirement related to any single component or combination of components illustrated therein. Additionally, various components depicted in FIGS. 3A and 3B may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A blood pump, comprising:
an impeller assembly housing;
an impeller assembly disposed within the impeller assembly housing and having an impeller configured to cause blood to flow through the pump;
a motor housing;
a motor disposed within the motor housing and configured to drive the impeller; and
a pivotable housing connector coupled, at a first end, to a distal end of the motor housing and, at a second end, to a proximal end of the impeller assembly housing, and
wherein the impeller assembly housing and the motor housing are configured to be delivered through an aorta of a patient;
wherein the pivotable housing connector comprises a first portion and a second portion, wherein the first portion is coupled to the second portion by a mechanical pivot joint.

2. The blood pump of claim 1, the pivotable housing connector comprising a flexible membrane.

3. The blood pump of claim 1, the motor comprising a driving magnet assembly and the impeller assembly comprising a driven magnet assembly coupled to the impeller and configured to rotate with the impeller, wherein the driving magnet assembly is configured to cause the driven magnet assembly to rotate.

4. A blood pump, comprising:
an impeller assembly housing;
an impeller assembly disposed within the impeller assembly housing and having an impeller configured to cause blood to flow through the pump;
a motor housing;
a motor disposed within the motor housing and configured to drive the impeller; and
a pivotable housing connector coupled, at a first end, to a distal end of the motor housing and, at a second end, to a proximal end of the impeller assembly housing, and
wherein the impeller assembly housing and the motor housing are configured to be delivered through an aorta of a patient;
the motor comprising a driving magnet assembly and the impeller assembly comprising a driven magnet assembly coupled to the impeller and configured to rotate with the impeller, wherein the driving magnet assembly is configured to cause the driven magnet assembly to rotate;
the driving magnet assembly comprising a primary driving surface and the driven magnet assembly comprising a primary driven surface, wherein the primary driving surface and primary driven surface are configured so that the driving magnet assembly and the driven magnet assembly achieve a maximum magnetic coupling when the impeller assembly housing is in a coupling position with respect to the motor housing.

5. The blood pump of claim 4, wherein when the impeller assembly is in the coupling position, the primary driving surface is parallel to the primary driven surface.

6. The blood pump of claim 5, further comprising a pivot stop configured to prevent the impeller assembly housing from moving beyond the coupling position.

7. The blood pump of claim 4, wherein the impeller assembly housing is configured to be moved into one or more additional coupling positions, each of the one or more additional coupling positions corresponding to a specified torque response.

8. A blood pump, comprising:
an impeller assembly housing;
an impeller assembly disposed within the impeller assembly housing and having an impeller configured to cause blood to flow through the pump;
a motor housing;
a motor disposed within the motor housing and configured to drive the impeller; and
a pivotable housing connector coupled, at a first end, to a distal end of the motor housing and, at a second end, to a proximal end of the impeller assembly housing, wherein the impeller assembly housing is configured to be moved into one or more coupling positions, each of the one or more coupling positions corresponding to a specified torque response.

9. The blood pump of claim 8, the pivotable housing connector comprising a mechanical pivot joint or a flexible membrane.

10. The blood pump of claim 8, the motor comprising a driving magnet assembly and the impeller assembly comprising a driven magnet assembly coupled to the impeller and configured to rotate with the impeller, wherein the driving magnet assembly is configured to cause the driven magnet assembly to rotate.

11. The blood pump of claim 10, the driving magnet assembly comprising a primary driving surface and the driven magnet assembly comprising a primary driven surface, wherein the primary driving surface and primary driven surface are configured so that the driving magnet assembly and the driven magnet assembly achieve a maximum magnetic coupling when the impeller assembly housing is in a first coupling position with respect to the motor housing.

12. The blood pump of claim 11, wherein when the impeller assembly is in the first coupling position, the primary driving surface is parallel to the primary driven surface.

13. The blood pump of claim 12, further comprising a pivot stop configured to hold the impeller assembly in each of the one or more coupling positions.

14. A blood pump, comprising:
an impeller assembly housing;
an impeller assembly disposed within the impeller assembly housing and having an impeller configured to cause blood to flow through the pump;
a motor housing;
a motor disposed within the motor housing and configured to drive the impeller; and
a pivotable housing connector coupled, at a first end, to a distal end of the motor housing and, at a second end, to a proximal end of the impeller assembly housing, wherein the pivotable housing connector comprises a flexible membrane, and wherein the pivotable housing connector is configured to accommodate a curvature of an aortic arch of a patient as the impeller assembly housing and the motor housing are delivered through an aorta of the patient;
wherein the impeller assembly housing is configured to be moved into one or more coupling positions, each of the one or more coupling positions corresponding to a specified torque response.

15. The blood pump of claim 14, the motor comprising a driving magnet assembly and the impeller assembly comprising a driven magnet assembly coupled to the impeller and configured to rotate with the impeller, wherein the driving magnet assembly is configured to cause the driven magnet assembly to rotate.

16. The blood pump of claim 15, the driving magnet assembly comprising a primary driving surface and the driven magnet assembly comprising a primary driven surface, wherein the primary driving surface and primary driven surface are configured so that the driving magnet assembly and the driven magnet assembly achieve a maximum magnetic coupling when the impeller assembly housing is in a coupling position with respect to the motor housing.

17. The blood pump of claim 14, the motor comprising a driving magnet assembly and the impeller assembly comprising a driven magnet assembly coupled to the impeller and configured to rotate with the impeller, wherein the driving magnet assembly is configured to cause the driven magnet assembly to rotate.

* * * * *